(12) United States Patent
Jenison

(10) Patent No.: US 9,008,788 B2
(45) Date of Patent: Apr. 14, 2015

(54) ENABLEMENT AND/OR DISABLEMENT OF AN EXPOSURE MODE OF AN IMPLANTABLE MEDICAL DEVICE

(75) Inventor: Troy A. Jenison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1434 days.

(21) Appl. No.: 12/703,223

(22) Filed: Feb. 10, 2010

(65) Prior Publication Data
US 2011/0196449 A1 Aug. 11, 2011

(51) Int. Cl.
| A61N 1/00 | (2006.01) |
| A61N 1/08 | (2006.01) |
| A61N 1/37 | (2006.01) |
| A61N 1/372 | (2006.01) |

(52) U.S. Cl.
CPC .............. *A61N 1/08* (2013.01); *A61N 1/3718* (2013.01); *A61N 1/37252* (2013.01); *A61N 1/37211* (2013.01)

(58) Field of Classification Search
USPC ................................................ 607/60, 2, 30
See application file for complete search history.

(56) References Cited

U.S. PATENT DOCUMENTS

| 7,082,328 B2 | 7/2006 | Funke |
| 7,460,912 B2 | 12/2008 | Hoyme et al. |
| 7,561,915 B1 | 7/2009 | Cooke et al. |
| 7,583,995 B2 | 9/2009 | Sanders |
| 7,623,930 B2 | 11/2009 | Zeijlemaker et al. |
| 7,660,620 B2 | 2/2010 | Zeijlemaker et al. |
| 2004/0267233 A1 | 12/2004 | Ginggen |
| 2005/0043761 A1 | 2/2005 | Connelly et al. |
| 2005/0070787 A1 | 3/2005 | Zeijlemaker |
| 2006/0025820 A1 | 2/2006 | Phillips et al. |
| 2006/0149331 A1 | 7/2006 | Mann et al. |
| 2006/0167496 A1* | 7/2006 | Nelson et al. ..................... 607/2 |
| 2006/0173295 A1 | 8/2006 | Zeijlemaker |
| 2006/0241392 A1 | 10/2006 | Feinstein et al. |
| 2006/0293591 A1 | 12/2006 | Wahlstrand et al. |
| 2007/0021814 A1 | 1/2007 | Inman et al. |
| 2007/0078497 A1 | 4/2007 | Vandanacker |

(Continued)

FOREIGN PATENT DOCUMENTS

| EP | 1935450 A1 | 6/2008 |
| WO | 2007/134143 A2 | 11/2007 |

OTHER PUBLICATIONS (PCT/US2011/024038) PCT Notification of Transmittal of the International Search Report and the Written Opinion of the International Searching Authority, Mailed Apr. 21, 2011, 10 pages.

*Primary Examiner* — Christopher D Koharski
*Assistant Examiner* — Roland Dinga
(74) *Attorney, Agent, or Firm* — Michael J. Ostrom

(57) ABSTRACT

This disclosure describes techniques for enabling and/or disabling an exposure operating mode using telemetry signals. A telemetry device may be configured to periodically transmit telemetry signals indicating presence of a source of a disruptive energy field in accordance with a communication protocol. An implantable medical device may be configured to receive the telemetry signals from the telemetry device and enter the exposure operating mode in response to receiving a first one of the telemetry signals indicating the presence of the source of the disruptive energy field. The implantable medical device may also exit the exposure operating mode in response to not receiving any of telemetry signals indicating the presence of the source of the disruptive energy field for a predetermined period of time.

40 Claims, 5 Drawing Sheets

(56) References Cited

U.S. PATENT DOCUMENTS

| | | |
|---|---|---|
| 2007/0238975 A1 | 10/2007 | Zeijlemaker |
| 2007/0255332 A1 | 11/2007 | Cabelka et al. |
| 2007/0265685 A1 | 11/2007 | Zeijlemaker |
| 2009/0138058 A1* | 5/2009 | Cooke et al. ............... 607/5 |
| 2010/0057153 A1 | 3/2010 | Ballis |

* cited by examiner

ENABLEMENT AND/OR DISABLEMENT OF AN EXPOSURE MODE OF AN IMPLANTABLE MEDICAL DEVICE

TECHNICAL FIELD

The disclosure relates generally to implantable medical devices and, in particular, to operation of an implantable medical device when exposed to a disruptive energy field.

BACKGROUND

A wide variety of implantable medical devices (IMDs) that deliver a therapy or monitor a physiologic condition of a patient have been clinically implanted or proposed for clinical implantation in patients. IMDs may deliver therapy or monitor conditions with respect to a variety of organs, nerves, muscles or tissues of the patients, such as the heart, brain, stomach, spinal cord, pelvic floor, or the like. In some cases, IMDs may deliver electrical stimulation therapy via one or more electrodes, which may be included as part of one or more elongated implantable medical leads.

For example, an implantable cardiac device, such as a cardiac pacemaker or implantable cardioverter-defibrillator, provides therapeutic stimulation to the heart by delivering electrical therapy signals such as pulses or shocks for pacing, cardioversion, or defibrillation via electrodes of one or more implantable leads. As another example, a neurostimulator may deliver electrical therapy signals, such as pulses, to a spinal cord, brain, pelvic floor or the like, to alleviate pain or treat symptoms of any of a number of neurological or other diseases, such as epilepsy, gastroparesis, Alzheimer's, depression, obesity, incontinence and the like.

Exposure of the IMD to a disruptive energy field may result in undesirable operation of the IMD. The IMD may be exposed to the disruptive energy field for any of a number of reasons. For example, one or more medical procedures may need to be performed on the patient within which the IMD is implanted. For example, the patient may need to have a magnetic resonance imaging (MRI) scan, computed tomography (CT) scan, electrocautery, diathermy, radio frequency (RF) ablation, or other medical procedure that produces a magnetic field, electromagnetic field, electric field or other disruptive energy field.

The disruptive energy field may induce energy on one or more of the implantable leads coupled to the IMD. The IMD may inappropriately detect the induced energy on the leads as physiological signals. Alternatively, or additionally, the induced energy on the leads may result in the inability to correctly detect physiological signals. In either case, detection of the induced energy on the leads as physiological signals may result in the IMD delivering therapy (e.g., a pacing pulse) when it is not desired or withholding therapy when it is desired. In other instances, the induced energy on the leads may result in heating of the tissue and/or nerve site adjacent to the electrodes of the leads. Such heating may compromise pacing and sensing thresholds at the tissue site, which could result in reduced therapy efficacy.

SUMMARY

This disclosure describes techniques for enabling and/or disabling an exposure operating mode via telemetry signals. A telemetry device may be configured to periodically transmit telemetry signals indicating presence of a source of a disruptive energy field in accordance with a communication protocol. An implantable medical device may receive the telemetry signals from the telemetry device and enter the exposure operating mode in response to receiving at least one of the telemetry signals indicating the presence of the source of the disruptive energy field. The implantable medical device may also exit the exposure operating mode in response to not receiving any of telemetry signals indicating the presence of the source of the disruptive energy field for a predetermined period of time.

In one example, this disclosure is directed to a system for configuring an implantable medical device in the presence of a disruptive energy field. The system includes a telemetry device that is configured to periodically transmit telemetry signals in accordance with a communication protocol indicating presence of a source of a disruptive energy field. The system also includes an implantable medical device that is configured to receive the telemetry signals from the telemetry device and transition from a first operating mode to a second operating mode that is less susceptible to undesirable operation in the disruptive energy field than the first operating mode in response to receiving a first one of the telemetry signals indicating the presence of the source of the disruptive energy field. The implantable medical device is further configured to operate in the second operating mode as long as the implantable medical device continues to receive telemetry signals indicating the presence of the source of the disruptive energy field and transition from the second operating mode to the first operating mode in response to not receiving any of the telemetry signals indicating the presence of the source of the disruptive energy field for a predetermined period of time.

In another example, this disclosure is directed to an implantable medical device that includes an antenna, a telemetry module configured to receive telemetry signals from a telemetry device via the antenna and a processor configured to transition the implantable medical device from a first operating mode to a second operating mode that is less susceptible to undesirable operation in a disruptive energy field in response to receiving a first telemetry signal indicating the presence of a source of a disruptive energy field. The processor is further configured to operate the implantable medical device in the second operating mode as long as the implantable medical device continues to receive telemetry signals indicating presence of the source of the disruptive energy field and transition from the second operating mode to the first operating mode in response to not receiving any telemetry signals indicating presence of the source of the disruptive energy field for a predetermined period of time.

In a further example, this disclosure is directed to method that includes receiving a telemetry signal indicating the presence of a source of the disruptive energy field and transitioning the implantable medical device from a first operating mode to a second operating mode that is less susceptible to undesirable operation in a disruptive energy field in response to receiving a first telemetry signal indicating the presence of the source of the disruptive energy field. The method also includes operating the implantable medical device in the second operating mode as long as the implantable medical device continues to receive telemetry signals indicating presence of the source of the disruptive energy field and transitioning the implantable medical device from the second operating mode to the first operating mode in response to not receiving any telemetry signals indicating presence of the source of the disruptive energy field for a predetermined period of time.

In another example, this disclosure is directed to an implantable medical device that includes means for receiving telemetry signals indicating the presence of a source of a disruptive energy field and means for transitioning the implantable medical device from a first operating mode to a second operating mode that is less susceptible to undesirable operation in the disruptive energy field in response to receiving a first telemetry signal indicating the presence of the source of the disruptive energy field. The implantable medical device also includes means for operating the implantable medical device in the second operating mode as long as the implantable medical device continues to receive telemetry signals indicating presence of the source of the disruptive energy field and means for transitioning the implantable medical device from the second operating mode to the first operating mode in response to not receiving any telemetry signals indicating presence of the source of the disruptive energy field for a predetermined period of time.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
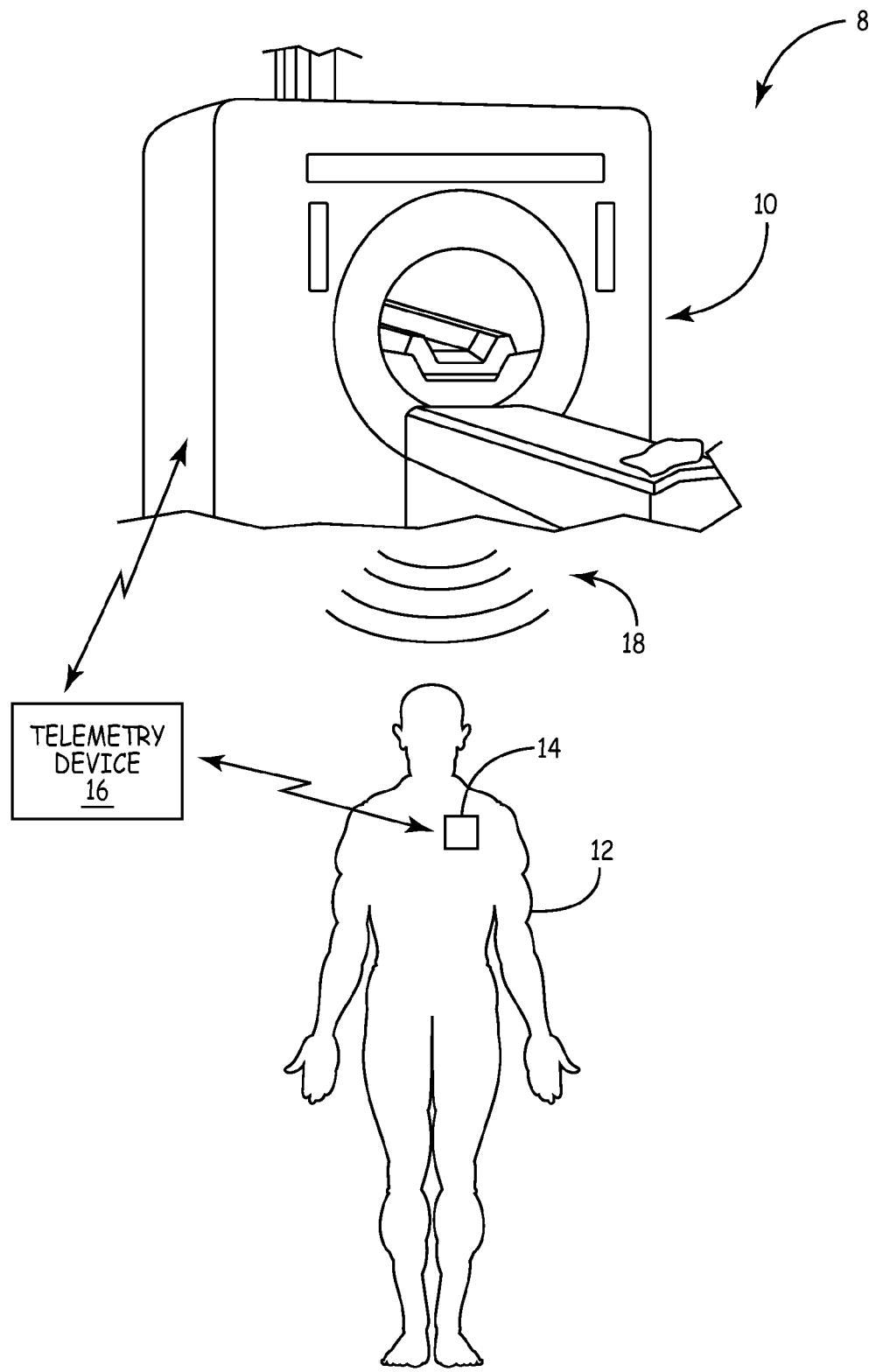
FIG. 1 is a conceptual diagram illustrating an environment in which an implantable medical device is exposed to a disruptive energy field.

FIG. 1 is a conceptual diagram illustrating an environment 8 that includes a magnetic resonance imaging (MRI) device 10, a patient 12 in which an implantable medical device (IMD) 14 is implanted, and a telemetry device 16 that communicates with IMD 14 in accordance with the techniques of this disclosure. Environment 8 may, for example, be an MRI suite at a medical facility.

MRI device 10 uses magnetic and radio frequency (RF) fields to produce images of body structures for diagnosing injuries and/or disorders. For example, MRI device 10 may generate a static magnetic field, gradient magnetic fields and/or RF fields. The static magnetic field is a non-varying magnetic field that is typically always present around MRI device 10 whether or not an MRI scan is in progress. Gradient magnetic fields are low-frequency pulsed magnetic fields that are typically only present while the MRI scan is in progress. RF fields are pulsed RF fields that are also typically only present while the MRI scan is in progress. The magnitude, frequency, timing or other characteristic of disruptive energy field 18 may vary based on the type of MRI scanner producing the field.

Some or all of the various types of fields produced by MRI device 10 may interfere with operation of IMD 14. In other words, one or more of the various types of fields produced by MRI device 10 may make up disruptive energy field 18. For example, the gradient magnetic fields or RF fields produced by MRI device 10 may induce energy on one or more of implantable leads of IMD 14. The induced energy on the leads or on other components of IMD 14 may be conducted to the tissue of patient 12 resulting in heating of the tissue adjacent to electrodes of the leads or adjacent to a housing of IMD 14. Such heating may compromise pacing and sensing thresholds at the tissue site, which could result in reduced therapy efficacy. In some instances, IMD 14 may inappropriately detect the induced energy on the leads as physiological signals, which may in turn cause IMD 14 to deliver undesired therapy or withhold desired therapy. In other instances, the induced energy on the leads may result in IMD 14 not detecting physiological signals that are actually present, which may again result in IMD 14 delivering undesired therapy or withholding desired therapy.

To reduce the undesirable effects of disruptive energy field 18, IMD 14 is capable of operating in a mode that is less susceptible to undesirable operation during exposure to disruptive energy field 18, referred to herein as the "exposure mode" or "exposure operating mode." In the case of an exposure operating mode that specifically accounts for MRI scans, the mode may be referred to as an MR Conditional mode or an MR Safe mode. IMD 14 may be configured from a normal operating mode (e.g., the current operating mode) to the exposure operating mode prior to being exposed or upon being exposed to disruptive energy field 18.

In accordance with one aspect of this disclosure, IMD 14 may transition from the normal operating mode to the exposure operating mode in response to receiving a telemetry signal or communication from telemetry device 16. As used herein, the terms telemetry signal and telemetry communication may be used interchangeably. Telemetry device 16 may, for example, be configured to periodically transmit a telemetry signal that indicates the presence of MRI device 10. The telemetry signal transmitted by telemetry device 16 is transmitted in accordance with a communication protocol designed for communication with IMD 14. Telemetry device 16 may broadcast this telemetry signal such that any IMD within range of telemetry device 16 and that communicates using the communication protocol transitions to the exposure operating mode in response to the signal.

After transitioning to the exposure operating mode in response to the received signal, IMD 14 may transmit a telemetry signal to telemetry device 16 to indicate that it is operating in the exposure operating mode. As such, the telemetry signal may be used as confirmation that IMD 14 is operating in the exposure operating mode. In instances in which IMD 14 is configured into the exposure operating mode manually before patient 12 enters environment 8, IMD 14 may transmit the confirmation telemetry signal in response to receiving the telemetry signal from telemetry device 16. Telemetry device 16 may generate an alert in response to receiving the telemetry signal from IMD 14 to confirm to an operator of MRI device 10 that IMD 14 is configured in the exposure operating mode. In this case, telemetry device 16 is capable of bi-directional communication with IMD 14. In other instances, telemetry device 16 may be a transmit-only device. Additionally, or alternatively, IMD 14 may send the telemetry signal to indicate IMD 14 is operating in the exposure operating mode to MRI device 10, which may provide an alert or modify operating in response to receiving the signal.

Telemetry device 16 may communicate with IMD 14 via wireless communication using any techniques known in the art. Examples of communication techniques may include RF telemetry, but other techniques are also contemplated. In some instances, telemetry device 16 and IMD 14 may communicate in the 402-405 MHz frequency band in accordance with the Medical Implant Communications Service (MICS) frequency band regulation. In other instances, telemetry device 16 and IMD 14 may communicate in the 401-402 MHz or 405-406 MHz frequency bands in accordance with the Medical External Data Service (MEDS) band regulations, in the unlicensed industrial, scientific and medical (ISM) band, or other regulated or unregulated frequency band.

After exposure of IMD 20 to disruptive energy field 18 or upon detection of serious medical event, it is desirable to reconfigure IMD 20 back to the normal operating mode. This may be especially desirable for IMDs for which sensing or therapy is suspended during the exposure operating mode. In some instances, IMD 20 may be automatically reconfigured to the normal operating mode. For example, IMD 20 may be automatically reconfigured to the normal operating mode in response to not receiving any of the periodic telemetry communications from telemetry device 16 for a predetermined amount of time. To this end, IMD 14 may continue to monitor for periodic telemetry signals from telemetry device 16 while operating in the exposure operating mode and exit the exposure operating mode in response to no longer receiving the periodic telemetry signals. In this manner, IMD 14 may enter and exit the exposure mode only during the period of time during which IMD 14 is within environment 8 and likely exposed to disruptive energy field 18 of MRI device 10. In other instances, IMD 14 may exit the exposure operating mode in response to one or more other conditions being met in addition to or instead of no longer receiving the periodic telemetry signals. For example, IMD 20 may be automatically reconfigured to the normal operating mode in response to expiration of a timer, in response to no longer detecting disruptive energy field 18 or other condition, or a combination of conditions. In further instances, IMD 20 may be manually reconfigured into the exposure operating by a user (e.g., physician or technician) interacting with a programmer.

Environment 8 may be a shielded room that does not allow RF signals in or out, as is the case in an MRI suite. As such, the periodic telemetry communications transmitted by telemetry device 16 would not interfere with other IMDs, such as IMDs implanted in patients located elsewhere in the medical facility. In other words, the IMDs not located within environment 8 are not be within the range of the broadcast transmission of telemetry device 16. Therefore, there is little risk of inadvertently programming another IMD into the exposure operating mode.

Telemetry device 16 may be a stand-alone device located within environment 8. For example, telemetry device 16 may be MRI labeled such that it remains in the MRI suite during the MRI scan. Alternatively, telemetry device 16 may be partially located within environment 8. For example, an antenna of telemetry device 16 may MRI labeled such that the antenna may be located within the MRI suite while the electronic components of telemetry device 16 are located outside of the MRI suite and electrically connected to the antenna. In other instances, some or all of telemetry device 16 may be integrated within MRI device 10.

IMD 14 is implanted within patient 12 to provide therapy to or to monitor a physiological condition of patient 12. IMD 14 may be any of a variety of therapy devices. For example, IMD 14 may be a device that provides electrical stimulation therapy via one or more implantable leads that include one or more electrodes (not shown). In some instances, IMD 14 may be a device that provides electrical stimulation therapy in the form of cardiac rhythm management therapy to a heart of patient 12 via leads implanted within one or more atria and/or ventricles of the heart. The cardiac rhythm management therapy delivered by IMD 14 may include pacing, cardioversion, defibrillation and/or cardiac resynchronization therapy (CRT). In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like.

In addition to providing electrical stimulation therapy, IMD 14 may sense one or more physiological parameters of patient 12. When one or more leads are implanted within the heart of patient 12, for example, electrodes of the leads may sense electrical signals attendant to the depolarization and repolarization of the heart to monitor a rhythm of the heart or detect particular heart conditions, e.g., tachycardia, bradycardia, fibrillation or the like. IMD 14 may sense a variety of other physiologic parameters or other parameters related to a condition of patient 12, including, for example, neurologic parameters, intracardiac or intravascular pressure, activity, posture, pH of blood or other bodily fluids or the like.

In other instances, IMD 14 may be a device that delivers a drug or therapeutic agent to patient 12 via a catheter. IMD 14 may deliver, e.g., using a pump, the drug or therapeutic agent to a specific location of patient 12. IMD 14 may deliver the drug or therapeutic agent at a constant or variable flow rate. Drug pumps, infusion pump or drug delivery devices may be used to treat symptoms of a number of different conditions. For example, IMD 14 may deliver morphine or ziconotide to reduce or eliminate pain, baclofen to reduce or eliminate spasticity, chemotherapy to treat cancer, or any other drug or therapeutic agent (including saline, vitamins, etc.) to treat any other condition and/or symptom of a condition.

Environment 8 of FIG. 1 illustrates MRI device 10 as the energy source that generates disruptive energy field 18 to which IMD 14 is exposed. However, the techniques may be used to control operation of IMD 14 within environments in which other sources of disruptive energy fields are present. For example, IMD 14 may operate in accordance with the techniques of this disclosure in environments in which disruptive energy field 18 is generated by a CT scanner, X-ray machine, electrocautery device, diathermy device, ablation device, radiation therapy device, electrical therapy device, magnetic therapy device or any other environment with medical devices that radiate energy to produce magnetic, electromagnetic, electric fields or other disruptive energy fields. As such, environment 8 may be a surgical room or other environment instead of a MRI suite. The techniques of this disclosure may also be used to operate IMD 14 within non-medical environments that include disruptive energy fields.

Figure 2:
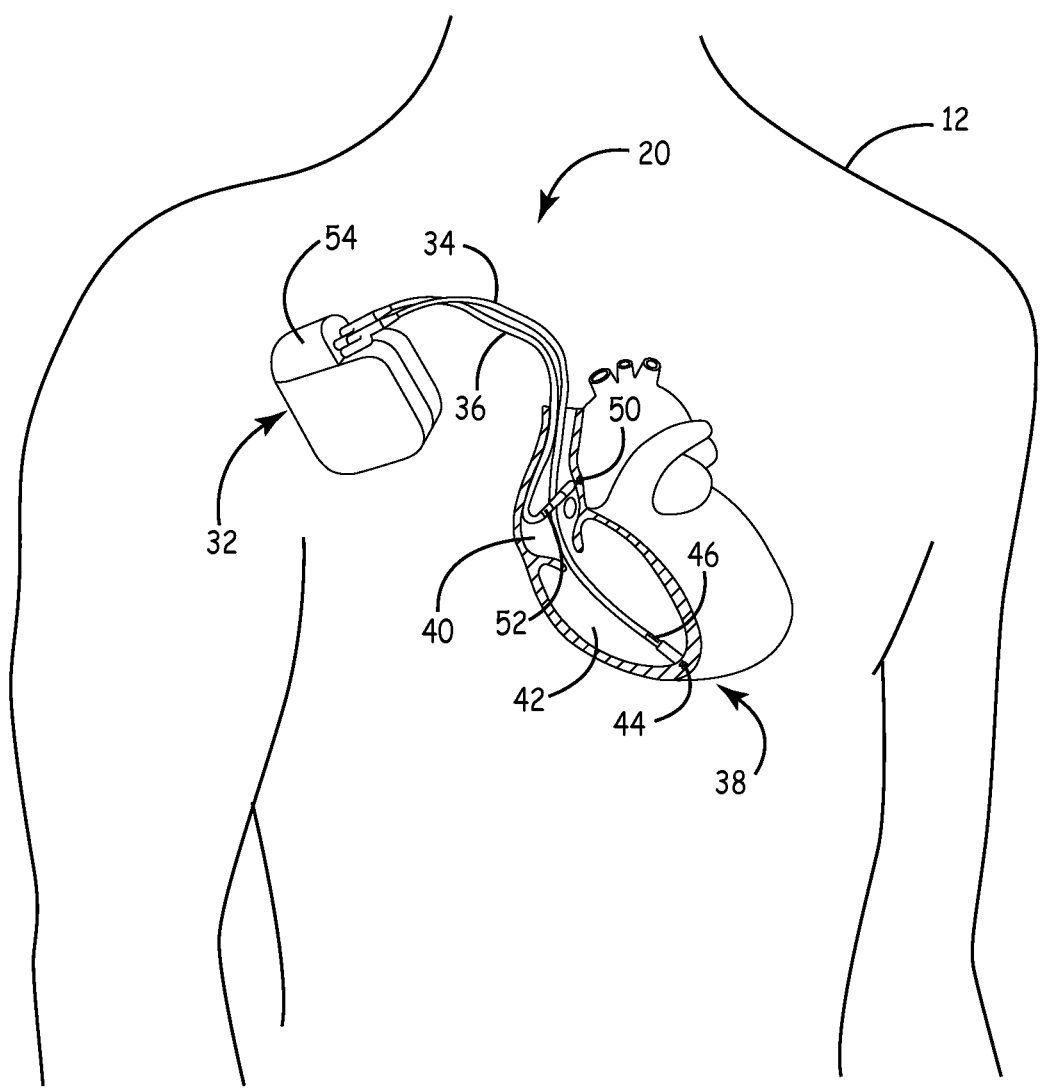
FIG. 2 is a conceptual diagram illustrating an example implantable medical device that may be used to provide therapy to patient.

FIG. 2 is a conceptual diagram illustrating an example IMD 20 that may be used to provide therapy to patient 12. IMD 20 includes a housing 32 and leads 34 and 36 that extend from housing 32. IMD 20 may, for example, correspond to IMD 14 of FIG. 1.

In the example illustrated in FIG. 2, IMD 20 is an implantable cardiac device that senses electrical activity of a heart 38 of patient 12 and/or provides electrical stimulation therapy to heart 38 of patient 12. The electrical stimulation therapy to heart 38, sometimes referred to as cardiac rhythm management therapy, may include pacing, cardioversion, defibrillation and/or cardiac resynchronization therapy (CRT). The combinations of cardiac therapies provided may be dependent on a condition of patient 12. In some instances, IMD 20 may provide no therapy to patient 12, but instead provide only sensing of electrical activity or other variable of heart 38, such as in the case of an implantable loop recorder.

In the illustrated example, lead 34 is a right ventricular (RV) lead that extends through one or more veins (not shown), the superior vena cava (not shown), and right atrium 40, and into right ventricle 42 of heart 38. Lead 34 includes electrodes 44 and 46 located along a distal end of lead 34. In the illustrated example, lead 36 is right atrial (RA) lead that extends through one or more veins and the superior vena cava, and into the right atrium 40 of heart 38. Lead 36 includes electrodes 50 and 52 located along a distal end of lead 36.

Electrodes 44 and 50 may take the form of extendable helix tip electrodes mounted retractably within an insulative electrode head (not shown) of respective leads 34 and 36. Electrodes 46 and 52 may take the form of ring electrodes. In other embodiments, electrodes 44, 46, 50 and 52 may be other types of electrodes. For example, electrodes 44, 46, 50 and 52 may all be ring electrodes located along the distal end of the associated lead 34 or 36. Additionally, either or both of leads 34 and 36 may include more than two electrodes or only a single electrode.

Each of the electrodes 44, 46, 50 and 52 may be electrically coupled to a respective conductor within the body of its associated lead 34 and 36. The respective conductors may extend from the distal end of the lead to the proximal end of the lead and couple to circuitry of IMD 20. For example, leads 34 and 36 may be electrically coupled to a stimulation module, a sensing module, or other modules of IMD 20 via connector block 54 of housing 32. In some examples, proximal ends of leads 34 and 36 may include electrical contacts that electrically couple to respective electrical contacts within connector block 54. In addition, in some examples, leads 34 and 36 may be mechanically coupled to connector block 54 with the aid of set screws, connection pins or another suitable mechanical coupling mechanism.

When IMD 20 is capable of delivering electrical stimulation therapy, IMD 20 delivers the therapy (e.g., pacing pulses) to heart 38 via any combination of electrodes 44, 46, 50 and 52 to cause depolarization of cardiac tissue of heart 38. For example, IMD 20 may deliver bipolar pacing pulses to right atrium 40 via electrodes 50 and 52 of lead 36 and/or may deliver bipolar pacing pulses to right ventricle 42 via electrodes 44 and 46 of lead 34. In another example, IMD 20 may deliver unipolar pacing pulses to atrium 40 and ventricle 42 using housing 32 as an electrode in conjunction with one of electrodes 44, 46, 50 and 52. The housing electrode may be formed integrally with an outer surface of the hermetically-sealed housing of IMD 20 or otherwise coupled to housing 32. In some examples, the housing electrode is defined by an uninsulated portion of an outward facing portion of housing 32 of IMD 20.

Electrodes 44, 46, 50 and 52 may also sense electrical signals attendant to the depolarization and repolarization of heart 38. The electrical signals are conducted to IMD 20 via one or more conductors of respective leads 34 and 36. IMD 20 may use any combinations of the electrodes 44, 46, 50, 52 or the housing electrode for unipolar or bipolar sensing. As such, the configurations of electrodes used by IMD 20 for sensing and pacing may be unipolar or bipolar depending on the application. IMD 20 may analyze the sensed signals to monitor a rhythm of heart 38 or detect an arrhythmia of heart 38, e.g., tachycardia, bradycardia, fibrillation or the like. In some instances, IMD 20 provides pacing pulses (or other therapy) to heart 38 based on the cardiac signals sensed within heart 38. In other words, pacing may be responsive to the sensed events.

As described above, exposure of IMD 20 to a disruptive energy field 18 may result in undesirable operation. For example, gradient magnetic or RF fields produced by MRI device 10 may induce energy on one or more conductors of respective ones of implantable leads 34 and 36 or on the housing electrode. In some instances, the induced energy on conductors of leads 34 or 36 or on components of IMD 20 results in heating of the tissue adjacent to electrodes 44, 46, 50 and 52 or housing 32 of IMD 20. Such heating may compromise pacing and sensing thresholds at the tissue, which could result in reduced therapy efficacy. In other instances, IMD 20 may inappropriately detect the induced energy on the conductors of leads 34 or 36 as physiological signals, which may in turn cause IMD 20 to deliver undesired therapy or withhold desired therapy. In further instances, the induced energy on the conductors of leads 34 or 36 may result in IMD 20 not detecting physiological signals that are actually present, which may again result in IMD 20 delivering undesired therapy or withholding desired therapy.

Configuring IMD 20 into an exposure operating mode may reduce the undesirable effects that may be caused by exposure to disruptive energy field 18. As such, IMD 20 may be configured to operate in the exposure operating mode prior to or immediately subsequent to entering environment 8 in which the disruptive energy field 18 is present. IMD 20 may, for example, be configured into the exposure operating mode in response to receiving one of the periodic telemetry communications transmitted from telemetry device 16 in accordance with the techniques of this disclosure. Additionally, IMD 20 exits the exposure operating mode using one of the techniques described herein.

The exposure operating mode is typically less susceptible to undesirable operation in disruptive energy field 18 than the normal operating mode. In other words, operating IMD 20 in the exposure mode may reduce some or all of the adverse effects caused by disruptive energy field 18. When operating in the exposure operating mode, IMD 20 is configured to operate with different functionality compared to the normal operating mode. In some instances, be configured to operate with reduced functionality.

For example, IMD 20 may operate in an exposure operating mode in which sensed signals (e.g., those caused by energy induced on the leads) do not affect delivery of therapy. If patient 12 is pacing dependent, for example, the exposure mode of IMD 20 may correspond to an asynchronous pacing mode with no sensing, e.g., AOO, VOO or DOO. In another example, the exposure mode of IMD 20 may correspond to an asynchronous pacing mode that includes sensing, but has no mode of response to the pacing, e.g., such as a AAO, AVO, ADO, VVO, VAO, VDO, DDO, DAO or DVO pacing mode. In either of these cases, pacing is provided with no modification due to sensing. As such, the induced energy on the leads caused by disruptive energy field 18 does not result in undesirable operation of IMD 20.

In another example, the exposure operating mode of IMD 20 may correspond to a sensing only mode, such as OAO, OVO or ODO, in which no pacing is provided. Such modes may only be used in cases in which patient 12 is not pacing dependent. Because there is no pacing in these pacing modes, such pacing modes may prevent IMD 20 from delivering undesirable stimulation or withholding desirable stimulation due to the induced energy on the leads.

The exposure mode may also suspend temporary operation of other functionality of IMD 20, particularly those that may function incorrectly when exposed to disruptive energy field 18. Some example functionality that may be suspended while operating in the exposure mode include tachycardia detection and therapy, fibrillation detection and therapy, impedance measurements, battery measurements, P- and R-wave measurements. Additional functionality that may be suspended while in the exposure mode includes collection of diagnostic data.

In other instances, IMD 20 may be operating with approximately the same functionality or even increased functionality in the exposure mode. For example, IMD 20 may use a different sensor or algorithm to detect cardiac activity of the heart of patient 12, such as pressure sensor measurements rather than electrical activity of the heart. As another example, IMD 20 may implement one or more filters that filter out the undesirable signals. In a further example, IMD 20 may implement one or more shunts or traps to redirect the energy away from the tissue adjacent to the electrodes.

IMD 20 illustrated in FIG. 2 is merely an example of a type of IMD within which the techniques of this disclosure may be used. In other examples, IMD 20 may include more or fewer leads. For example, IMD 20 may include three leads, e.g., a third lead implanted within a left ventricle of heart 38. In another example, IMD 20 may include only a single lead that is implanted within either an atrium or ventricle of heart 38. As such, IMD 20 may be used for single chamber or multi-chamber cardiac rhythm management therapy.

In addition to more or fewer leads, each of the leads may include more or fewer electrodes. In instances in which IMD 20 is used for therapy other than pacing, e.g., defibrillation or cardioversion, the leads may include elongated electrodes, which may, in some instances, take the form of a coil. IMD 20 may deliver defibrillation or cardioversion shocks to heart 38 via any combination of the elongated electrodes and housing electrode. As another example, IMD 20 may include leads with a plurality of ring electrodes, e.g., as used in some implantable neurostimulators.

In still other examples, a medical system may include epicardial leads and/or patch electrodes instead of or in addition to the transvenous leads 34 and 36 illustrated in FIG. 2. Further, IMD 20 need not be implanted within patient 12. In examples in which IMD 20 is not implanted in patient 12, IMD 20 may deliver electrical stimulation therapy to heart 38 via percutaneous leads that extend through the skin of patient 12 to a variety of positions within or outside of heart 38.

The techniques of this disclosure are described in the context of cardiac rhythm management therapy for purposes of illustration. The techniques of this disclosure, however, may be used to operate an IMD that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 3:
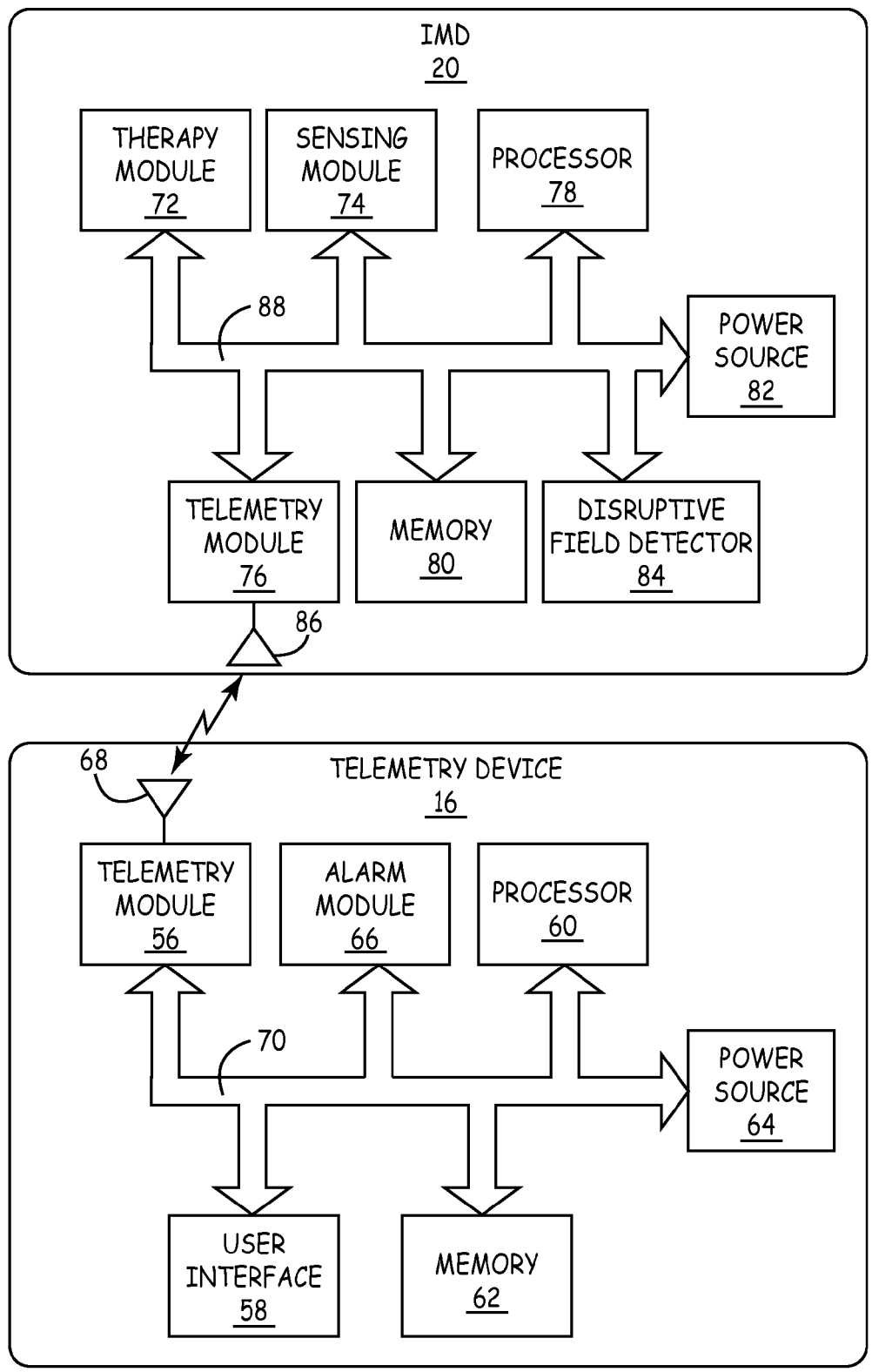
FIG. 3 is a functional block diagram of an example configuration of components of the implantable medical device of FIG. 2.

FIG. 3 is a block diagram illustrating telemetry device 16 and IMD 20 in further detail. Telemetry device 16 includes a telemetry module 56, user interface 58, processor 60, memory 62, power source 64 and alert module 66. IMD 20 includes a therapy module 72, sensing module 74, telemetry module 76, processor 78, memory 80, power source 82, and disruptive field detector 84. The components of telemetry device 16 and IMD 20 may be interconnected by data buses 70 and 88, respectively, or by one or more direct electrical connections.

As described above, telemetry device 16 may be configured to periodically transmit a telemetry signal indicating the presence of MRI device 10 or other source of a disruptive energy field 18. Telemetry module 56 may broadcast this telemetry signal via antenna 68 such that any IMD within range of telemetry device 16 and that communicates using the communication protocol receives the telemetry signal. In other instances, telemetry device 16 may be able to identify all of the IMDs within range and present a list of IMDs to a user (e.g., physician) who may then select the one or more IMDs to be reprogrammed. In this case, the periodic telemetry communications may be sent only to the one or more IMDs identified by the user to be reprogrammed, thereby preventing the inadvertent reprogramming of incorrect IMDs.

The telemetry signal transmitted by telemetry module 56 is transmitted in accordance with a communication protocol designed for communication with IMD 20. The telemetry signal transmitted by telemetry module 56 may conform to the specifications of a proprietary communication protocol. In other instances, the telemetry signal may conform to the specifications of a non-proprietary communication protocol, such as a protocol assigned by a standards organization (e.g., Institute of Electrical and Electronics Engineers (IEEE), International Organization for Standardization (ISO), International Telecommunication Union—Telecommunication Standardization Sector (ITU-T), International Telecommunication Union—Radiocommunication Sector (ITU-R), or Internet Engineering Task Force (IETF)).

In general, the communication protocol is a set of standards for communicating data between devices over a communication channel. The communication protocol may, for example, define standards for data representation, signaling, authentication, error detection or the like. The communication protocol may be broken down into layers that define characteristics for the distinct communication layers. In one example, the layers may be modeled on one or more of the layers defined by the International Open System Interconnect (OSI) reference model, although the layers may be adapted as needed. The OSI reference model defines a physical layer, a data link layer, a network layer, a transport layer, a session layer, a presentation layer and an application layer.

The telemetry communications transmitted by telemetry module 56 indicate the presence of MRI device 10 or other source of a disruptive energy field 18. The telemetry communications may include a special message structure such that IMD 20 recognizes the telemetry signal as an indication of the presence of MRI device 10. In one example, the telemetry communication may include one or more dedicated bits in a control field of a packet to indicate the presence of MRI device 10. In another example, the telemetry communication may include one or more bits in a data field of a packet to indicate the presence of MRI device 10. In one example, the telemetry communication may include a single designated bit that is asserted to indicate presence of the source of disruptive energy field 18, e.g., MRI device 10 in the example of FIG. 1. In other words, the telemetry communication indicates the presence of MRI device 10 when the designated bit is set or asserted (e.g., equal to "1") and indicates MRI device 10 is not present when the designated bit is not set or asserted (e.g., equal to "0").

In another example, the telemetry communication may include a plurality of designated bits that are configured to indicate the presence of the source of disruptive energy field 18. In the case of the plurality of designated bits, the telemetry communication may be used to specify a particular type of source or environment. For instance, the designated bits may be set to a first value to indicate a first environment (e.g., environment 8 of FIG. 1) and set to a second value to indicate a second environment (e.g., an RF ablation surgical environment or a different MRI environment). In the case of the special message structure including two designated bits, for example, value "00" may be a default value indicating that no source of disruptive energy field 18 is present, a value of "01" may indicate that a first type of MRI device is present, a value of "10" may indicate that an RF ablation device is present, and a value of "11" may indicate that a second type of MRI device is present. The special message structure may include more than two designated bits and may indicate the presence of other types of sources of disruptive energy field 18 in addition to or instead of MRI devices and RF ablation devices.

In one embodiment, telemetry module 56 periodically generates a wakeup communication that indicates the presence of MRI device 10. To this end, telemetry module 56 may include a wakeup communication module (not shown). Telemetry module 56 may generate a wakeup communication (which may include one or more wakeup packets) in accordance with the communication protocol and set the designated bit(s) in the control or data field of each of the wakeup packets. In one example, telemetry device 16 transmits the plurality of wakeup packets for a period of time that exceeds a wakeup interval of telemetry module 76 of IMD 20.

When patient 12 enters environment 8, IMD 20 implanted within patient 12 receives at least one of the wakeup packets indicating presence of MRI device 10 (or other source of disruptive energy field 18) via telemetry module 76 and antenna 86. In one instance, telemetry module 76 of IMD 20 may be configured to operate in a low power state (sometimes referred to as a sleep state) in which a receiver of telemetry module 76 is periodically powered up to monitor for a wakeup communication. Operating telemetry module 76 of IMD 20 in the low power state when no communication session is established reduces the amount of power consumed by telemetry module 76 when no telemetry is occurring. This may extend a service life of power source 82 of IMD 20.

Conventionally, the wakeup communication is used to transition telemetry module 76 of IMD 20 to a high power state such that a communication can be established with IMD 20. In accordance with one aspect of this disclosure, however, one or more designated bits in the wakeup communication may be set to indicate to IMD 20 the presence of MRI device 14. Processor 78 may begin to operate IMD 20 in the exposure operating mode in response to receiving the wakeup communication in which the designated bit(s) are set. Processor 78 may, for example, include a mode selection module (not shown) that retrieves the operating parameters of the exposure operating mode from memory 80 and begins operating in accordance with the retrieved parameters. In instances in which the designated bits also identify a type of source of disruptive energy field 18, processor 78 may select the operating parameters of an exposure operating mode corresponding to the particular type of source. In any case, telemetry module 76 may not establish a communication session when the designated bit(s) are set. Instead, telemetry module 76 of IMD 20 continues to operate in the low power state and periodically powers up to monitor for additional wakeup communications. In this manner, the telemetry communication with the special message structure functions as a "if you hear this message you are in an MRI environment." When the designated bit(s) in the wakeup communication are not set or set to a default value indicating no presence of a source of disruptive energy field 18, telemetry module 76 may transition to the high power state to establish a communication session as conventionally done in response to a wakeup communication.

In other instances, telemetry device 16 and IMD 20 may use a native communication mode instead of the wakeup communication mode. For example, telemetry device 16 may transmit one or more open request packets with the designated bit(s) set to indicate presence of MRI device 10. As such, conventional packets used in the native communication mode for telemetry functions (e.g., establishing a communication channel) may be modified to serve a non-telemetry function, which in this case is causing IMD to enter the exposure operating mode.

The native communication mode may have a more complex encoding scheme, faster transmission or data rate, larger packet sizes and/or more complex packet structures than the wakeup communication mode. In one example, the wakeup communication mode uses Manchester encoding, a data rate of 6.4 Kbps, a packet size of 25 bytes and the packet includes content bytes and MAC bytes while the native communication mode uses DQPSK or DBPSK encoding, a data rate of greater than 48 Kbps, a packet size of greater than 47 bytes and a packet structure that includes control, content, reed Solomon and MAC bytes. As such, the amount of power consumed by telemetry module 76 while operating in the native communication mode is typically larger than when operating in a wakeup communication mode.

In response to transitioning to the exposure operating mode, processor 78 may cause telemetry module 76 may transmit a telemetry communication to confirm that IMD 20 is operating in the exposure mode. If the transition to the exposure operating mode is unsuccessful, processor 78 may cause telemetry module 76 to transmit a telemetry communication to indicate that the transition was unsuccessful. The telemetry communication from telemetry module 76 may also be sent in accordance with the telemetry communication protocol. Telemetry module 76 may broadcast the telemetry communication such that any receiver within range of IMD 20 receives the telemetry communication, e.g., telemetry device 16 and/or MRI device 10 in the example of FIG. 1. In other instances, telemetry module 76 may transmit the telemetry communication to telemetry device 16 from which telemetry module 76 received the telemetry communication indicating presence of MRI device 10.

When the telemetry communication from IMD 20 indicates the transition to the exposure operating mode was a success, telemetry device 16 and/or MRI device 10 may generate an alert or other notification to confirm to the operator of MRI device 10 or patient 12 that IMD 20 is in the exposure operating mode. When the telemetry communication from IMD 20 indicates the transition to the exposure operating mode was a success, telemetry device 16 and/or MRI device 10 may also generate an alert or other notification to indicate to the operator of MRI device 10 or patient 12 that IMD 20 is not operating in the exposure operating mode. Telemetry device 16 of FIG. 3, for example, includes an alarm module 66 that generates the alert or notification. The alert or notification may, for example, be a visual indicator (e.g., light) that is initiated in response to the confirmation telemetry communication from IMD 20 indicating that IMD 20 is in the exposure operating mode. In this manner, the operator and/or patient 12 may be confident that IMD 20 is in the MR Conditional or MR Safe mode.

After exposure of IMD 20 to disruptive energy field 18 or upon occurrence of a serious medical event, it is desirable to reconfigure IMD 20 back to the normal operating mode. In one example, processor 78 may automatically reconfigure IMD 20 to the normal operating mode in response to not receiving any of the periodic telemetry communications from telemetry device 16 for a predetermined amount of time. Telemetry module 76 may continue to monitor for telemetry communications with the designated bit(s) set during the exposure operating mode. Because telemetry device 16 may continue to periodically transmit the telemetry communications indicating presence of MRI device 10, telemetry module 76 should continue to receive the periodic telemetry communications during the MRI scan or while otherwise remaining in environment 8. Upon exiting environment 8, telemetry module 76 will no longer receive the periodic telemetry communications from telemetry device 16.

Processor 78 or telemetry module 76 may include a timer or other mechanism to track the amount of time since last receiving a periodic communication from telemetry device 16. The timer or other mechanism will be reset upon receiving a periodic communication from telemetry device 16. The predetermined amount of time may be preconfigured, e.g., upon implant or prior to entering environment 10. In other instances, the predetermined amount of time may be specified in the periodic telemetry communication from telemetry device 16. The predetermined time interval may, in one example, be between fifteen and forty-five minutes. However, the predetermined amount of time may be longer or shorter depending on the application.

The condition of patient 12 may be continually monitored during the medical procedure, e.g., during the MRI scan, electrocautery, ablation or the like. In some instances, processor 78 and/or sensing module 74 may continue to monitor the condition of patient 12 during the exposure operating mode. In other instances, the condition of patient 12 may be monitored by one or more sensors that are not associated with IMD 20, (e.g., external sensors or other implanted sensors), or by a watchful eye of a physician performing the procedure (e.g., in the case of a surgery).

In cases in which IMD 20 continues to monitor the condition of patient 12, processor 78 may generate a notification to indicate the detection of a serious medical event, such as ventricular fibrillation. In one example, processor 78 may transmit a communication to telemetry device 16 via telemetry module 76 and antenna 86 to indicate that a serious medical event has been detected. In response to the communication, telemetry device 16 may generate an alert to a user of MRI device 10 (or other device) notifying the user of the detected medical event. In one example, the alert may be an audible and/or visual alert provided via user interface 58 of telemetry device 16.

In addition to providing the alert, telemetry device 16 may also stop transmitting the periodic communications. The telemetry device 16 may automatically stop transmitting the periodic communications in response to the detected medical event, in response to the communication from IMD 20, or in response to the user interacting with user interface 58. User interface 58 may, for example, include an emergency button that the user may actuate to cause telemetry device 16 to stop transmitting the periodic signals. In any case, ceasing the transmission of the periodic telemetry signals will cause telemetry module 76 of IMD 20 to no longer receive the periodic telemetry communications from telemetry device 16 and transition from the exposure operating mode to the normal operating mode after not receiving a communication for the predetermined period of time. In the normal operating mode, therapy module 72 may provide therapy to patient 12 to attempt to terminate the medical event (e.g., deliver a defibrillation shock in the case of ventricular fibrillation).

In other aspects, it may be undesirable to wait for the predetermined period of time before transitioning IMD 20 from the exposure operating mode to the normal operating mode. As such, the emergency button may cause the telemetry module 56 to send an emergency communication to IMD 20 causing IMD 20 to immediately revert back to the normal operating mode. For example, the emergency communication may be a communication with different special structure, e.g., another designated bit(s) set within the data or control field, recognizable by IMD 20. In another example, the emergency communication may be the same as the communication indicating the presence of MRI device 10, but with the designated bit(s) no longer set or set to a default value indicating no presence of disruptive energy field 18.

In other instances, processor 78 may cause IMD 20 may exit the exposure operating mode in other manners. For example, processor 78 may automatically reconfigure IMD 20 to the normal operating mode in response to expiration of a timer, in response to disruptive field detector 84 no longer detecting disruptive energy field 18, or occurrence or non-occurrence of other condition, or a combination of conditions. Disruptive field detector 84 may include one or more sensors located within or otherwise coupled to IMD 20. The one or more sensors of disruptive field detector 84 may include an RF sensor, a magnetic field detector, such as a Hall sensor or a reed switch, or sensor or combination of sensors. In some instances, disruptive field detector 84 may be within housing 32 of IMD 20. For example, disruptive field detector 84 may be the same field detector used to sense a magnetic programming head of a programming device. Alternatively, IMD 20 may be coupled to a disruptive field detector 84 located outside of housing 32 of IMD 20. Processor 78 may analyze the outputs of the one or more sensors individually or in combination (e.g., by weighting the outputs of the sensors or other blending the outputs of the sensors) to detect the presence or absence of disruptive energy field 18. In another example, processor 78 may manually reconfigure IMD 20 into the exposure operating by a user (e.g., physician or technician) interacting with a programmer.

Telemetry module 56 of telemetry device 16 communicates wirelessly with telemetry module 76 of IMD 20 by any of a number of wireless communication techniques. Example wireless communication techniques include RF telemetry, but other techniques are also contemplated. To this end, telemetry module 56 and telemetry module 76 may include any suitable hardware, firmware, software or any combination thereof for wireless communication. For example, telemetry module 56 and telemetry module 76 may include appropriate modulation, demodulation, frequency conversion, filtering, and amplifier components for transmission and/or reception of data.

Telemetry device 16 of FIG. 3 also may include a user interface 58 via which a user may interact with telemetry device 16. User interface 58 may include an input mechanism, such as a keypad, a peripheral pointing device, a touch screen, microphone or the like, and an output mechanism, such as a display (e.g., a cathode ray tube (CRT) display, a liquid crystal display (LCD) or light emitting diode (LED) display), speaker or the like. In some instances, alarm module 66 may be integrated as part of user interface 58.

Telemetry device 16 also includes a processor 60 that controls operation of the components of telemetry device 16. Telemetry device 16 further includes a memory 62. Memory 62 may include computer-readable instructions that, when executed by processor 60, cause telemetry device 16 to perform various functions attributed to telemetry device 16 herein.

IMD 20 of FIG. 3 includes a sensing module 74 and a therapy module 72. As such, IMD 20 illustrated in FIG. 3 may provide both sensing and therapy functionality. Although FIG. 3 includes both sensing module 74 and therapy module 72, IMD 20 may only provide sensing functionality and no therapy as in the case of an implantable loop recorder. In such cases, IMD 20 may not include therapy module 72. Alternatively, IMD 20 may provide therapy with no sensing. In such cases, IMD 20 may not include sensing module 74.

Sensing module 74 is configured to monitor one or more physiological signals using one or more sensors connected to sensing module 74. In one example, sensing module 74 is configured to monitor signals sensed by one or more of electrodes on leads extending from IMD 20. In another example, sensing module 74 may be configured to monitor signals sensed by a sensor within or on IMD 20. In a further example, sensing module 74 may be configured to receive signals sensed by one or more wireless or lead-less sensors and transmitted wirelessly to IMD 20. The one or more sensors may sense physiological signals such as heart activity (e.g., electrocardiogram (ECG) signals), muscle activity (e.g., electromyography (EMG) signals), brain electrical activity (e.g., electroencephalography (EEG) signals), heart rate, intravascular pressure, blood pressure, blood flow, acceleration, displacement, motion, respiration, or blood/tissue chemistry such as oxygen saturation, carbon dioxide, pH, protein levels, enzyme levels or other parameter.

Sensing module 74 may store the sensed signals in memory 80. In some instances, sensing module 74 may store the sensed signals in raw form. In other instances, sensing module 74 may process the sensed signals and store the processed signals in memory 80. For example, sensing module 74 may amplify and filter the sensed signal and store the filtered signal in memory 80. The signals stored by sensing module 74 may, in some cases, be retrieved and further processed by processor 78.

IMD 20 may also provide therapy, such as electrical stimulation therapy or drug delivery therapy, to patient 12 in accordance with parameters of one or more selected therapy programs. In particular, processor 78 controls therapy module 72 to deliver therapy to patient 12 according to one or more therapy programs, which may be received from telemetry device 16 and stored in memory 80. In the case of electrical stimulation therapy, therapy module 72 may include a stimulation generator that generates and delivers electrical stimulation therapy, e.g., in the form of pulses or shocks. Processor 78 may control the stimulation generator to deliver electrical stimulation pulses with amplitudes, pulse widths, frequency, and/or electrode polarities specified by the one or more therapy programs. In the case of drug delivery therapy, therapy module 72 may include a pump that delivers a drug or therapeutic agent to patient 12. Processor 78 may control the pump to deliver the drug or therapeutic agent with the dosage and frequency (or rate) specified by the one or more therapy programs.

Power source 82 of IMD 20 delivers operating power to the components of telemetry device 16. Power source 82 may include a rechargeable or non-rechargeable battery. A non-rechargeable battery may be selected to last for several years, while a rechargeable battery may be charged from an external charging device on a daily or weekly basis. In either case, and especially in the case of the non-rechargeable battery, the amount of power of the battery is limited before requiring recharging or replacement.

Processor 78 may control operation of IMD 20, e.g., by controlling operation of the various components of IMD 20. Memory 80 may include computer-readable instructions that, when executed by processor 78, cause IMD 20 to perform various functions attributed to the components of telemetry device 16 herein. Memory 80 may also store sensed data and operating parameters received via telemetry from telemetry device 16. In instances in which IMD 20 may operate in a plurality of different exposure operating modes (e.g., based on the type of source of disruptive energy field 18), memory 80 may store a mapping that maps different values of the designated bits to corresponding exposure operating modes designed for the particular type of source.

Processors 60 and 78 may include one or more of a microprocessor, a controller, a DSP, an ASIC, an FPGA, or equivalent discrete or integrated logic circuitry. In some examples, processors 60 and 78 may include multiple components, such as any combination of one or more microprocessors, one or more controllers, one or more DSPs, one or more ASICs, or one or more FPGAs, as well as other discrete or integrated logic circuitry. The functions attributed to processors 60 and 78 herein may be embodied as software, firmware, hardware or any combination thereof. Memory 62 and 80 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media or a combination thereof.

IMD 20 and telemetry device 16 are illustrated for exemplary purposes. IMD 20 and telemetry device 16 may include more or fewer components than shown in FIG. 3 depending on the application of the devices. As such, the techniques described in this disclosure should not be limited by the example devices illustrated in FIG. 3.

Figure 4:
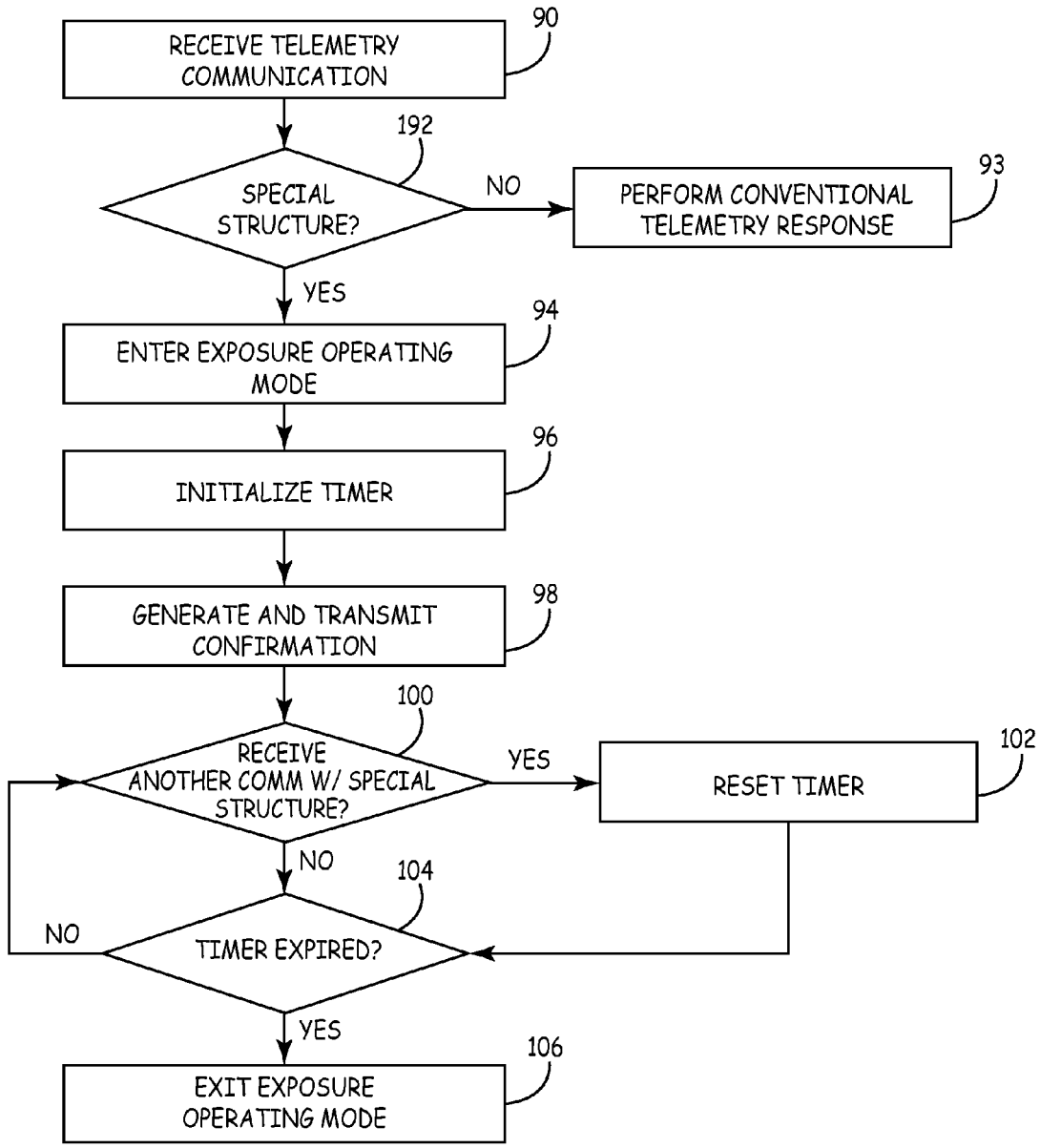
FIG. 4 is a flow diagram illustrating example operation of an implantable medical device in accordance with one aspect of this disclosure.

FIG. 4 is a flow diagram illustrating example operation of IMD 20 in accordance with one aspect of this disclosure. Initially, telemetry module 76 of IMD 20 receives a telemetry communication (90). Telemetry module 76 may receive the telemetry communication in the native communication mode or in the wakeup communication mode.

Telemetry module 76 or processor 78 determines whether the telemetry communication has the special message structure or format indicating presence of MRI device 10 (92). Telemetry module 76 or processor 78 may, for example, determine whether the designated bit(s) within the communication have been set to indicate the presence of MRI device 10. If telemetry module 76 or processor 78 determines that the telemetry communication does not have the special message structure (e.g., the designated bit(s) are not set) ("NO" branch of block 92), telemetry module 76 performs the conventional telemetry operation in response to the packet (93). In the case of a wakeup packet, for example, processor 78 may transition telemetry module 76 from the wakeup communication mode to the native communication mode to listen for native mode packets from an external device (e.g., programmer). In the case of a native mode open request, telemetry module 76 may reply with an open response packet.

If telemetry module 76 or processor 78 determines that the telemetry communication does not have the special message structure (e.g., the designated bit(s) are set) ("YES" branch of block 92), processor 78 configures IMD 20 to enter the exposure operating mode (94). In some instances, the special message structure may further identify a particular type of source of disruptive energy field 18 and processor 78 may select an exposure operating mode corresponding to the type of source based on the value of the designated bits. As described above, the exposure operating mode is less susceptible to undesirable operation in the disruptive energy field than the normal operating mode.

Telemetry module 76 or processor 78 may initialize a timer to track the amount of time that has elapsed since last receiving a telemetry communication with the special message structure (96). In one instance, the telemetry communication sent from telemetry device 16 may specify the time to which initialize the timer. In this case, the specified time may be the periodicity at which telemetry device 16 transmits the periodic communications indicating presence of MRI device 10.

Telemetry module 76 may generate and transmit one or more telemetry communications to confirm that IMD 20 is operating in the exposure operating mode (98). In other instances, telemetry module 76 may not transmit the confirmation signals, in which case block 98 is skipped. Telemetry module 76 or processor 78 continues to monitor for additional telemetry communications with the special message structure (100). When telemetry module 76 or processor 78 receives another telemetry communication with the special message structure ("YES" branch of block 100), telemetry module 76 or processor 78 resets the timer tracking the amount of time that has elapsed since last receiving a telemetry communication with the special message structure (102).

When telemetry module 76 or processor 78 does not receive another telemetry communication with the special message structure ("NO" branch of block 100), telemetry module 76 or processor 78 determines whether the timer is expired (104). In the case of a count down timer, the timer may be expired upon reaching zero. In the case of a count up timer, the timer may be expired upon reaching a threshold value. When the timer is not expired ("NO" branch of block 104), telemetry module 76 or processor 78 continues to monitor for another telemetry communication with the special message structure. When the timer has expired ("YES" branch of block 104), processor 78 causes IMD 20 to exit the exposure operating mode (106). In this manner, IMD 20 exits the exposure operating mode in response to no longer receiving telemetry communications from telemetry device 16 for a particular period of time.

Figure 5:
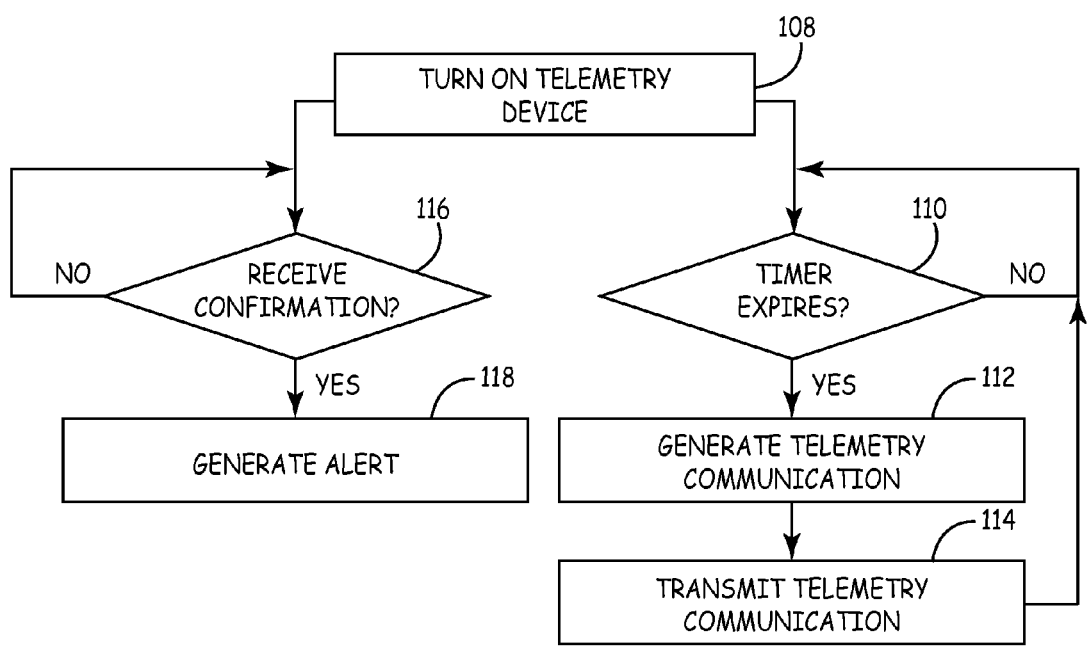
FIG. 5 is a flow diagram illustrating example operation of a telemetry device in accordance with another aspect of this disclosure.

FIG. 5 is a flow diagram illustrating example operation of telemetry device 16 in accordance with another aspect of this disclosure. Initially, telemetry device 16 is turned on (108). Telemetry device 16 determines whether a timer that tracks the amount of time since last transmitting a telemetry communication with the special message structure expires (110). When the timer has not expired ("NO" branch of block 110), telemetry device 16 continues to monitor the timer.

When the timer has expired ("YES" branch of block 110), telemetry device 16 generates a telemetry signal with the special message structure to indicate the presence of MRI device 10 or other source of a disruptive energy field 18 (112). The telemetry communication is generated in accordance with a communication protocol and may, in some instances, include one or more dedicated bit(s) in a control field or data field of the packet to indicate the presence of MRI device 10. The telemetry signal may be a wakeup communication or a native mode communication. Telemetry device 16 transmits the generated telemetry communication (114). Telemetry module 56 of telemetry device 16 may, for example, broadcast the telemetry communication via antenna 68 such that any IMD within range of telemetry device 16 and that communicates using the communication protocol receives the telemetry signal.

In some instances, telemetry device 16 may also be capable of receiving a confirmation signal from IMD 20. As such, telemetry device 16 may determine whether a confirmation signal has been received (116). If a confirmation signal has not been received ("NO" branch of block 116), telemetry device 16 continues to monitor for the confirmation signal. If a confirmation signal is received ("YES" branch of block 116), telemetry device 16 generates a confirmation alert to confirm that IMD 20 is operating in the exposure operating mode (118). In other instances, telemetry device 16 may be a transmit only device. In this case, steps 116 and 118 are not performed.

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A system for configuring an implantable medical device in the presence of a disruptive energy field, the system comprising:

a telemetry device that is configured to periodically transmit wireless telemetry signals in accordance with a wireless communication protocol indicating presence of a source of a disruptive energy field; and an implantable medical device that is separate from the telemetry device and is configured to receive the wireless telemetry signals from the telemetry device, transition from a first operating mode to a second operating mode that is less susceptible to undesirable operation in the disruptive energy field in response to receiving a first one of the periodic wireless telemetry signals indicating the presence of the source of the disruptive energy field, operate in the second operating mode as long as the implantable medical device continues to receive periodic wireless telemetry signals indicating the presence of the source of the disruptive energy field, and transition from the second operating mode to the first operating mode in response to not receiving any of the periodic wireless telemetry signals indicating the presence of the source of the disruptive energy field for a predetermined period of time.

2. The system of claim 1, wherein the wireless telemetry signals include one or more designated bits to indicate the presence of the source of the disruptive energy field.

3. The system of claim 2, wherein the wireless telemetry signals include a single designated bit that indicates presence of the source of the disruptive energy field when asserted and indicates no presence of the source of the disruptive energy field when not asserted.

4. The system of claim 2, wherein the wireless telemetry signals include a plurality of designated bits that are configurable to indicate the presence of a particular type of source of disruptive energy field.

5. The system of claim 4, wherein the implantable medical device includes a memory that stores a plurality of exposure operating modes that each correspond with a different type of source of disruptive energy field and the implantable medical device selects the one of the plurality of exposure operating modes that corresponds with the particular type of source identified by the designated bits of the communication as the second operating mode.

6. The system of claim 1, wherein
the telemetry device transmits a communication indicating that the source of the disruptive energy field is no longer present; and
the implantable medical device transitions from the second operating mode to the first operating mode immediately after receiving the communication indicating that the source of the disruptive energy field is no longer present.

7. The system of claim 6, wherein the telemetry device receives an indication that a patient in which the implantable medical device is implanted is experiencing a serious medical event and the telemetry device transmits the communication indicating that the source of the disruptive energy field is no longer present in response to the indication.

8. The system of claim 7, wherein the telemetry device includes an emergency button and the telemetry device receives the indication that the patient is experiencing the serious medical event upon actuation of the emergency button.

9. The system of claim 7, wherein the telemetry device includes a receiver and the telemetry device receives the indication upon receiving a telemetry communication indicating that the patient is experiencing the serious medical event.

10. The system of claim 1, wherein
the implantable medical device transmits a wireless telemetry signal to the telemetry device in response to transitioning to the second operating mode; and
the telemetry device receives the wireless telemetry signal from the implantable medical device and generates an alert to confirm that the implantable medical device is operating in the second operating mode that is less susceptible to undesirable operation in a disruptive energy field.

11. The system of claim 10, wherein the telemetry device includes a visual indicator that provides a visual confirmation in response to receiving the wireless telemetry signal from the implantable medical device.

12. The system of claim 1, wherein the telemetry device is incorporated within the source of the disruptive energy field.

13. The system of claim 1, wherein the telemetry device is a stand-alone device that is magnetic resonance imaging (MRI) labeled.

14. The system of claim 1, wherein the telemetry device periodically transmits wireless wakeup telemetry signals to indicate presence of the source of the disruptive energy field.

15. The system of claim 14, wherein the implantable medical device operates in a low power state in which in which a telemetry module is periodically powered up to monitor for wireless wakeup telemetry signals, continues to operate in the low power state and periodically power up to monitor for additional wakeup communications when the wireless wakeup telemetry signal indicates the presence of the source of the disruptive energy field and transitions to a high power state in which the telemetry module is continually powered up to establish a communication session in accordance with the communication protocol when the wireless telemetry signal does not indicate presence of the source of the disruptive energy field.

16. The system of claim 1, wherein the source of the disruptive energy field is a magnetic resonance imaging (MRI) device.

17. The system of claim 1, wherein the implantable medical device includes a timer that tracks the amount of time that has elapsed since receiving a last wireless telemetry signal indicating the presence of the source of the disruptive energy field, wherein the timer resets upon receiving a subsequent periodic wireless telemetry signal indicating the presence of the source of the disruptive energy field, wherein the implantable medical device continues to operate in the second operating mode until timer indicates that the amount of time that has elapsed since receiving a last wireless telemetry signal is greater than the predetermined period of time.

18. An implantable medical device comprising:
an antenna;
a telemetry module configured to receive wireless telemetry signals from a telemetry device via the antenna; and
a processor configured to transition the implantable medical device from a first operating mode to a second operating mode that is less susceptible to undesirable operation in a disruptive energy field in response to receiving a first wireless telemetry signal indicating the presence of a source of a disruptive energy field, operate the implantable medical device in the second operating mode as long as the implantable medical device continues to receive wireless telemetry signals indicating presence of the source of the disruptive energy field, and transition from the second operating mode to the first operating mode in response to not receiving any wireless telemetry signals indicating presence of the source of the disruptive energy field for a predetermined period of time.

19. The implantable medical device of claim 18, wherein the wireless telemetry signals include one or more designated bits to indicate the presence of the source of the disruptive energy field.

20. The implantable medical device of claim 19, wherein the wireless telemetry signals include a single designated bit that indicates presence of the source of the disruptive energy field when asserted and indicates no presence of the source of the disruptive energy field when not asserted.

21. The implantable medical device of claim 19, wherein the wireless telemetry signals include a plurality of designated bits that are configurable to indicate the presence of a particular type of source of disruptive energy field.

22. The implantable medical device of claim 21, further comprising a memory that stores a plurality of exposure operating modes that each correspond with a different type of source of disruptive energy field,
wherein the processor is configured to select the one of the plurality of exposure operating modes that corresponds with the particular type of source identified by the designated bits of the communication as the second operating mode.

23. The implantable medical device of claim 18, wherein the processor is configured to transition from the second operating mode to the first operating mode immediately after receiving a communication indicating that the source of the disruptive energy field is no longer present.

24. The implantable medical device of claim 18, further comprising a sensing module that receives sensed physiological signals,
  wherein the processor detects a serious medical event based on analysis of the sensed physiological signals and controls the telemetry module to transmit a telemetry communication indicating that the patient is experiencing the serious medical event in response to the detection.

25. The implantable medical device of claim 18, wherein the processor controls the telemetry module to transmit a wireless telemetry signal confirming that the implantable medical device is operating in the second operating mode.

26. The implantable medical device of claim 18, wherein the telemetry module of the implantable medical device operates in a low power state in which the telemetry module is periodically powered up to monitor for wireless telemetry signals and continues to operate in the low power state to monitor for additional signals when the wireless telemetry signal indicates presence of the source of the disruptive energy field.

27. The implantable medical device of claim 26, wherein the telemetry module transitions from the low power state to a high power state in which the telemetry module is continually powered up to establish a communication session when the wireless telemetry signal does not indicate presence of the source of the disruptive energy field.

28. The implantable medical device of claim 18, wherein the source of the disruptive energy field is a magnetic resonance imaging (MRI) device.

29. The implantable medical device of claim 18, wherein the implantable medical device includes a timer that tracks the amount of time that has elapsed since receiving a last wireless telemetry signal indicating the presence of the source of the disruptive energy field, wherein the timer resets upon receiving a subsequent periodic wireless telemetry signal indicating the presence of the source of the disruptive energy field, wherein the processor is configured to continue to operate the implantable medical device in the second operating mode until timer indicates that the amount of time that has elapsed since receiving a last wireless telemetry signal is greater than the predetermined period of time.

30. A method for configuring an implantable medical device in the presence of a disruptive energy field, the method comprising:
  receiving a wireless telemetry signal indicating the presence of a source of the disruptive energy field;
  transitioning the implantable medical device from a first operating mode to a second operating mode that is less susceptible to undesirable operation in a disruptive energy field in response to receiving a first wireless telemetry signal indicating the presence of the source of the disruptive energy field;
  operating the implantable medical device in the second operating mode as long as the implantable medical device continues to receive wireless telemetry signals indicating presence of the source of the disruptive energy field; and
  transitioning the implantable medical device from the second operating mode to the first operating mode in response to not receiving any wireless telemetry signals indicating presence of the source of the disruptive energy field for a predetermined period of time.

31. The method of claim 30, wherein receiving the wireless telemetry signal indicating the presence of the source of the disruptive energy field comprises receiving a wireless telemetry signal having one or more designated bits to indicate the presence of the source of the disruptive energy field.

32. The method of claim 31, wherein the wireless telemetry signals include a single designated bit, the method further comprising:
  determining whether the designated bit is asserted;
  determining that the wireless telemetry signal indicates presence of the source of the disruptive energy field when it is determined that the designated bit is asserted; and
  determining that the wireless telemetry signal indicates no presence of the source of the disruptive energy field when the designated bit is not asserted.

33. The method of claim 30, wherein the wireless telemetry signals include a plurality of designated bits that are configurable to indicate the presence of a particular type of source of disruptive energy field, the method comprising:
  storing operating parameters of a plurality of exposure operating modes that each correspond with a different type of source of disruptive energy field;
  determining the type of source of the disruptive energy field based on the plurality of designated bits; and
  selecting the one of the plurality of exposure operating modes that corresponds with the particular type of source identified by the reality of designated bits of the communication as the second operating mode.

34. The method of claim 30, further comprising:
  receiving a communication indicating that the source of the disruptive energy field is no longer present; and
  transitioning from the second operating mode to the first operating mode immediately after receiving the communication indicating that the source of the disruptive energy field is no longer present.

35. The method of claim 30, further comprising:
  detecting a serious medical event based on analysis of one or more sensed physiological signals;
  transmitting a telemetry communication indicating that the patient is experiencing the serious medical event in response to detecting the medical event.

36. The method of claim 30, further comprising transmitting a wireless telemetry signal from the implantable medical device to confirm that the implantable medical device is operating in the second operating mode.

37. The method of claim 30, further comprising:
  operating a telemetry module of the implantable medical device in a low power state in which the telemetry module is periodically powered up to monitor for wireless telemetry signals;
  when the wireless telemetry signal indicates presence of the source of the disruptive energy field, continuing to operate the telemetry module of the implantable medical device in the low power state to periodically power up to monitor for additional wireless telemetry signals indicating the presence of the source of the disruptive energy field; and
  when the wireless telemetry signal does not indicate presence of the source of the disruptive energy field, transitioning the telemetry module from the low power state to a high power state in which the telemetry module is continually powered up to establish a communication session in accordance with the communication protocol.

38. The method of claim 30, further comprising:
  maintaining a timer to track the amount of time that has elapsed since receiving a last wireless telemetry signal indicating the presence of the source of the disruptive energy field;

resetting the timer upon receiving a subsequent wireless telemetry signal indicating the presence of the source of the disruptive energy field;

wherein operating the implantable medical device in the second operating mode as long as the implantable medical device continues to receive wireless telemetry signals indicating presence of the source of the disruptive energy field comprises operating the implantable medical device in the second operating mode when the timer does not indicate that the amount of time that has elapsed since receiving a last wireless telemetry signal is greater than the predetermined period of time; and transitioning the implantable medical device from the second operating mode to the first operating mode in response to not receiving any wireless telemetry signals indicating presence of the source of the disruptive energy field for a predetermined period of time comprises transitioning the implantable medical device from the second operating mode to the first operating mode in response to the timer indicates that the amount of time that has elapsed since receiving a last wireless telemetry signal is greater than the predetermined period of time.

39. An implantable medical device comprising:

means for receiving wireless telemetry signals indicating the presence of a source of a disruptive energy field;

means for transitioning the implantable medical device from a first operating mode to a second operating mode that is less susceptible to undesirable operation in the disruptive energy field in response to receiving a first wireless telemetry signal indicating the presence of the source of the disruptive energy field;

means for operating the implantable medical device in the second operating mode as long as the implantable medical device continues to receive wireless telemetry signals indicating presence of the source of the disruptive energy field; and means for transitioning the implantable medical device from the second operating mode to the first operating mode in response to not receiving any wireless telemetry signals indicating presence of the source of the disruptive energy field for a predetermined period of time.

40. The implantable medical device of claim 39, further comprising means for tracking the amount of time that has elapsed since receiving a last wireless telemetry signal indicating the presence of the source of the disruptive energy field, wherein:

the means for tracking is reset upon receiving a subsequent wireless telemetry signal indicating the presence of the source of the disruptive energy field, and the means for transitioning transitions the implantable medical device from the second operating mode to the first operating mode in response to transitioning the means for tracking the amount of time that has elapsed since receiving a last wireless telemetry signal being greater than the predetermined period of time.

* * * * *